United States Patent

Pfoh

[11] Patent Number: 5,291,402
[45] Date of Patent: Mar. 1, 1994

[54] HELICAL SCANNING COMPUTED TOMOGRAPHY APPARATUS

[75] Inventor: Armin H. Pfoh, New Berlin, Wis.

[73] Assignee: General Electric Company, Milwaukee, Wis.

[21] Appl. No.: 926,987

[22] Filed: Aug. 7, 1992

[51] Int. Cl.⁵ .............................................. G06F 15/42
[52] U.S. Cl. ......................... 364/413.14; 364/413.13; 364/413.15; 364/413.16; 364/413.18; 364/413.19
[58] Field of Search ............ 364/413.14, 413.15, 364/413.19, 413.13, 413.16, 413.18

[56] References Cited

U.S. PATENT DOCUMENTS

| | | | |
|---|---|---|---|
| 4,630,202 | 12/1986 | Mori | 364/414 |
| 4,965,726 | 10/1990 | Heuscher et al. | 364/413.19 |
| 5,032,990 | 7/1991 | Eberhard et al. | 364/413.15 |
| 5,046,003 | 9/1991 | Crawford | 364/413.15 |

Primary Examiner—Roy N. Envall, Jr.
Assistant Examiner—Gita D. Shingala
Attorney, Agent, or Firm—Quarles & Brady

[57] ABSTRACT

An x-ray computed tomography system for helical scanning, translates a patient as projections of the patient at various beam angles are obtained and employs a detector array having multiple rows displaced along the direction of translation. The intensity signals from the multiple rows are combined to produce a composite projection having an improved beam profile along the translation direction. The composite projection is generated by adding together intensity signals obtained for detector elements in each column, at a given beam angle, and for related columns measuring rays having angles differing by x radians or an integer multiple thereof. The intensity signals are selected so that their points of acquisition cluster closely about the position of the desired slice plane.

8 Claims, 4 Drawing Sheets

HELICAL SCANNING COMPUTED TOMOGRAPHY APPARATUS

BACKGROUND OF THE INVENTION

This invention relates to computed tomography ("CT") systems where the patient is moved continuously during the scanning and more specifically to a CT system employing multiple rows of detector elements displaced along the axis of patient movement.

X-RAY COMPUTED TOMOGRAPHY

Figure 1:
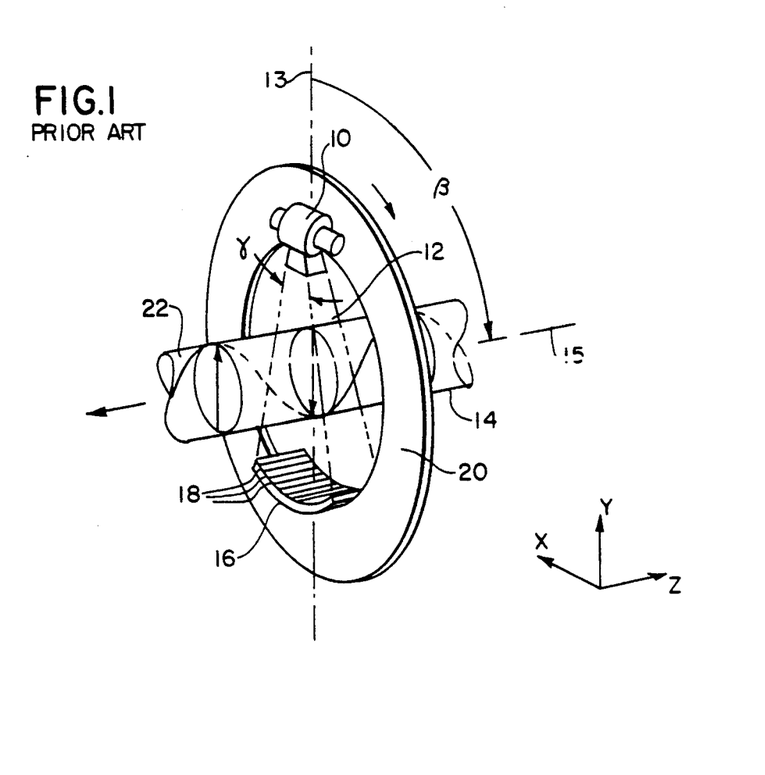
FIG. 1 is a pictorial representation of a prior art CT gantry with an imaged object showing the helical scanning of a fan beam and the relative angles and axes associated therewith as discussed in the Background of the Invention above.

Referring to FIG. 1, in a prior art x-ray computed tomography system, an x-ray source 10 is collimated to form a generally planar fan beam 12, along a beam axis 13. The fan beam is orientated to lie within the x-y plane of a Cartesian coordinate system, termed the "imaging plane", and diverges about the beam axis 13 within the imaging plane with a defined fan beam angle $\gamma$.

The fan beam 12 projects through an imaged object 14 to an x-ray detector array 16 also lying within the imaging plane. The detector array 16 is comprised of a large number of adjacent detector elements 18' which each measure the intensity of transmitted radiation along a different ray extending between the x-ray source 10 and that particular detector element 18. The detector elements 18 can be organized along an arc each to intercept x-rays from the x-ray source 10 along a different ray of the fan beam 12.

The x-ray source 10 and detector array 16 may be rotated on a gantry 20 within the imaging plane, around an axis of rotation 15, ordinarily within the imaged object 14, so that the fan beam 12 intercepts the imaged object 14 at different gantry angles $\beta$. At a number of gantry angles $\beta$, projections are acquired each comprised of the intensity signals from each of the detector elements 18. The intensity signals are a function of the attenuation of the fan beam 12 along each ray by the imaged object 14. The gantry 20 is then rotated to a new angle $\beta$ and the process is repeated to collect a number of projections at different angles $\beta$ to form a tomographic projection set.

The acquired tomographic projection set is typically stored in numerical form for computer processing to "reconstruct" a slice image according reconstruction algorithms known in the art such as "filtered backprojection". The reconstructed slice images may be displayed on a conventional CRT tube (not shown) or may be converted to a film record by means of a computer controlled camera (not shown).

A typical computed tomographic study entails the imaging of a series of slices of the imaged object 14 at slice planes parallel to the imaging plane. Each slice is displaced incrementally along a z-axis perpendicular to the x and y axes, so as to provide a third spatial dimension of information. A user may visualize this third dimension by viewing the slice images in order of position along the z-axis, or the numerical data comprising the set of reconstructed slices may be compiled by computer programs to produce shaded, perspective representations of the imaged object in three dimensions.

As the resolving power of computed tomography methods increases, narrower fan beams 12 and detector arrays 16 are employed and additional slices may be taken in the z-dimension. The time and expense of a tomographic study increases with the number of slices required. Longer scan times increase the discomfort to the patient, who must remain nearly motionless to preserve the fidelity of the tomographic reconstructions, and increase the chance of image artifacts caused by voluntary or involuntary movement. Longer scan times also decrease patient throughput and adversely affect the number of scans that may be obtained with an x-ray tube. For these reasons, there is considerable interest in reducing the time required to obtain a slice series.

The time required to collect the data for a series of slices depends in part on four components: a) the time required to accelerate the gantry to scanning speed, b) the time required to obtain a complete tomographic projection set, c) the time required to decelerate the gantry and d) the time required to reposition the patient in the z-axis for the next slice. Reducing the time required to obtain a full slice series may be accomplished by reducing the time required to complete any of these four steps.

The time required for acceleration and deceleration of the gantry may be avoided in tomographic systems that use slip rings rather than cables to communicate with the gantry. The slip rings permit continuous rotation of the gantry. Hereafter, it will be assumed that the CT systems discussed are equipped with slip rings or the equivalent to permit continuous rotation of over 360°.

The time required to acquire the tomographic data set is more difficult to reduce. Present CT systems require on the order of one to two seconds to acquire the projection set for one slice. This scan time may be reduced by rotating the gantry at a faster speed. A higher gantry speed, in general, will reduce the signal-to-noise ratio of the acquired data by the square root of the factor of rotational rate increase. This may be overcome to some extent in transmission tomography devices by increasing the radiation output of the x-ray tube, but is subject to the power limits of such devices.

A reduction in patient repositioning time may be accomplished by translating the patient in the z-axis synchronously with the rotation of the gantry. Referring still to FIG. 1, the combination of constant patient translation along the z-axis during the rotation of the gantry 20 and acquisition of projection data, has been termed "helical scanning" and refers to the apparent helical path 22 of the beam axis 13 with respect to the imaged object 14. The "pitch" of the helix, being the z-axis distance traversed by the imaged object 14 for one complete revolution of the gantry, is generally set equal to the width of the slices of which images will be reconstructed, and is generally related to the width of the fan beam 12 and detector array 16 along the z-axis. As used herein, "helical scanning" shall refer generally to the use of continuous translation of the patient or imaged object during the acquisition of tomographic imaging data, as opposed to "stop and shoot" scanning which will refer to the acquisition of the tomographic data set without translation of the patient or imaged object during the acquisition of a projection set.

HELICAL CT SCANNING

Continuous translation of the imaged object during scanning shortens the total scanning time required, for the acquisition of a given number of slices, by eliminating the length of time normally required for repositioning the patient between scans. Unfortunately, helical scanning may also introduce certain errors in the data of the acquired tomographic projection sets.

The mathematics of tomographic reconstruction assumes that the tomographic projection set is acquired along a constant z-axis slice plane. The helical scan path clearly deviates from this condition and this deviation results in image artifacts in the reconstructed slice image if there is any significant change in the object along the z-axis. The severity of the image artifacts depends generally on the "helix offset" in the projection data, measured as the difference between the table locations of the scanned data and the z axis value of the desired slice plane. Errors resulting from helical scanning will be referred to collectively as "skew" errors.

Several methods have been used to reduce skew errors in helical scanning. A first approach disclosed in U.S. Pat. No. 5,046,003, issued Sep. 3, 1991, entitled "Method for Reducing Skew Image Artifacts in Helical Projection Scanning", assigned to the same assignee as the present invention, and hereby incorporated by reference, uses non-uniform table motion to concentrate the helically acquired projections near the slice plane while limiting the accelerative forces on the patient. One disadvantage to this approach is that the slice planes must be determined before the scanning takes place.

A second approach, typified by co-pending U.S. patent applications Ser. No. 07/430,371 now U.S. Pat. No. 4,941,415 issued Jul. 17, 1990 filed No. 2, 1989, entitled: "Computerized Tomographic Image Reconstruction Method for Helical Scanning", and Ser. No. 07/435,980 now U.S. Pat. No. 5,233,518, issued Aug. 3, 1993, filed Nov. 13, 1989 entitled: "Extrapolative Reconstruction Method for Helical Scanning", assigned to the same assignee as the present invention, and incorporated by reference, skew artifacts are reduced by interpolating and/or extrapolating between the data of projection sets acquired at different gantry angles and hence at different z-axis positions with respect to the imaged object 14. The interpolation process provides effective projection data at a fixed slice plane and over a range of gantry angles $\beta$ despite the fact that each projection is in fact acquired at a different slice plane for each of the gantry angles $\beta$ because of the helical scanning.

A drawback to interpolation and extrapolation in correcting helically scanned data is that these processes reduce the resolution of the acquired projection data along the z-axis by increasing the effective beam profile along the z-axis. The spatial resolution of a CT system is a measure of the smallest object that may be resolved by the CT system; all other conditions being equal, higher resolution (the ability to image smaller objects) is preferred.

Figure 2A:
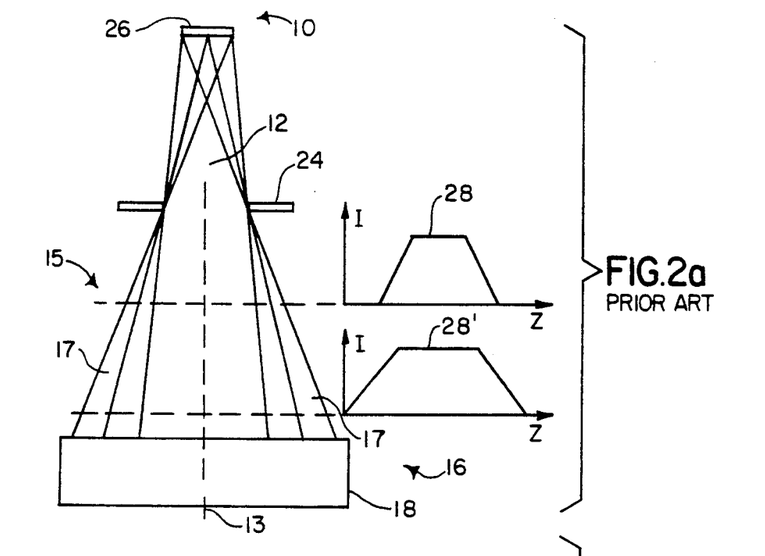
FIG. 2(a) is an exaggerated cross-section of the fan beam of FIG. 1 showing a penumbra caused by a collimator.

Referring to FIG. 2(a), the resolution of the projection data along the z-axis is determined generally by the width of the fan beam and by the geometry of the fan beam 12 and detector array 16. Fan beams that are wider along the z-axis produce images of lower resolution along the z-axis. In a prior art system, a focal spot 26 from which the fan beam 12 emanates and within the x-ray source 10, will have a finite z-axis extent, generally, on the order of one millimeter or more. X-rays emanate from the focal spot 26 at a relatively wide range of angles and are collimated by x-ray opaque blades of collimator 24. The blades of collimator 24 together form a slot generating the desired width of the fan beam 12 in the z-axis direction.

After the collimation by collimator 24, the fan beam 12 will typically diverge along to the z-axis, before striking the face of a given detector element 18. The z-axis extent of the focal spot 26 is finite and the blades of the collimator 24 are necessarily displaced from the detector element 18, therefore the effective width of the fan beam 12 along the z-axis, and hence the z-axis resolution of the system, will thus vary somewhat depending on how far one moves from the focal spot 26 toward the detector element 18.

The width of fan beam 12 may be characterized by its intensity profile 28 which plots x-ray intensity versus z-axis position as measured by the axis of rotation. The intensity of the fan beam shown by profile 28, drops off at its z-axis extremes as a result of a "penumbra effect" caused by the finite axis extent of the focal spot 26. Specifically, points within the fan beam 12 in a penumbra 17 at either z-axis extreme of the fan beam 12 are illuminated by less than the full area of the focal spot 26 as a result of progressive shadowing of the blades of the collimator 24. As a result of the penumbra effect, the intensity profile 28 of the radiation will be generally trapezoidal with the intensity falling at either z-axis extreme. This tailing off of intensity at the edges of the fan beam 12 is undesirable to the extent that it increases the width of the intensity profile 28. For increasingly narrow fan beams 12 the penumbra effect becomes more significant and as a practical matter, therefore, the penumbra effect limits the minimum practical z-axis width of the fan beam 12 and hence the z-axis resolution of the CT system.

At the surface of the detector elements 18, the fan beam 12 and the penumbra 17 widen to produce an intensity profile 28' similar to intensity profile but stretched along the z-axis to substantially span the z-axis width of the detector elements 18.

Figure 2B:
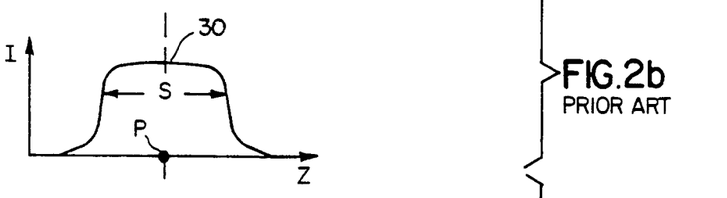
FIG. 2(b) is a graphical representation of the slice profile produced by the fan beam of FIG. 2(a)

Referring to FIG. 2(b), a slice profile 30 plots the signal developed by each detector element 18 as a function of z-axis position along the face of the element 18. The slice profile 30 will be the product of the intensity profile 30 times a function giving the sensitivity of the detector element 18 with z-axis position. Generally the sensitivity of the detector element 18 also falls off at its z-axis limits so that values of the slice profile 30 drop rapidly for positions in the penumbra 17 which are coincidentally near the edge of the detector element 18. The z-axis resolution of the scanning system will generally be considered to be the width of this profile 30 at half of its maximum value (Full Width Half Maximum or FWHM) designated "s".

Figure 2C:
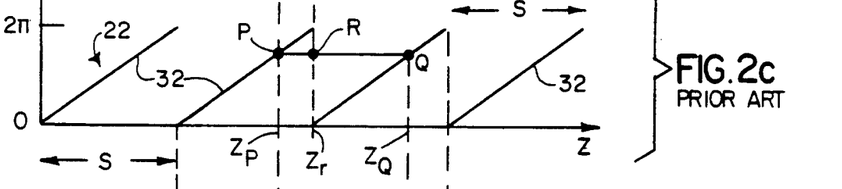
FIG. 2(c) is a graphical representation of the trajectory of the center of the fan beam of FIG. 2(a), with helical scanning, along the z-dimension with increasing gantry angle $\beta$.

Referring now to FIG. 2(c), in helical scanning, the beam axis 13 of the fan beam 12 will progress along the z-axis with respect to the imaged object 14 as the beam axis 13 rotates through different gantry angles $\beta$ as shown by trajectory 32. Ordinarily the pitch of the helical scan, i.e., the amount of z-axis translation for each 360° of gantry rotation, is set equal to the FWHM of profile 30 or s.

The interpolation of projection data acquired in a helical scan recognizes the general equivalence of projections taken at different z positions but at gantry angles $\beta$ differing by 360° or $2\pi$ radians. Accordingly, after every $2\pi$ (or 360°) of gantry angle $\beta$, the trajectory 32 is mapped to angles $\beta$ between 0 and $2\pi$. Nevertheless, the gantry angle $\beta$ should be understood, in fact, to increase monotonically, with the trajectory 32 being a continuous straight line.

Figure 2D:
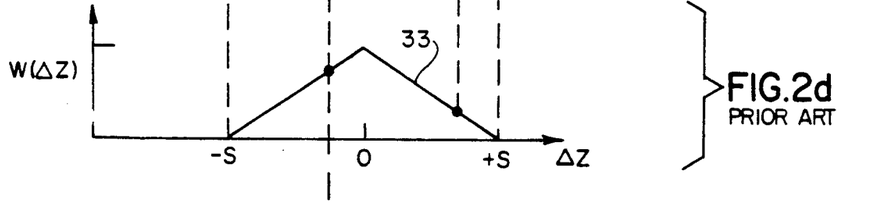
FIG. 2(d) is a graphical representation of a weighting function used for interpolation to reduce the effects of skew error in the helical scanning of FIG. 2(c)

An interpolated projection set at a slice plane $Z_r$, having projection data for a full range of gantry angles from 0 to $2\pi$ is obtained by selecting projection data at points P and Q at gantry angles differing by $2\pi$ and at z-axis positions on either side of the slice plane $Z_r$. Data for the point R in the slice plane $Z_r$ may then be interpolated from the data at points P and Q. The interpolation is performed by weighting the data of each projection P and Q by a weighting factor which is a function on the distance between the slice plane $Z_r$ and the z-axis positions of each of points P and Q and summing the weighted projection data at points P and Q together. Specifically, for a given gantry angle $\beta$ and a slice plane $Z_r$, the value of the projection at R in the slice plane $Z_r$ is:

$$R(Z_r, \beta) = w(\Delta Z_p)P(Z_p, \beta) + w(\Delta Z_q)Q(Z_q, \beta) \quad (1)$$

where $\Delta Z_p$ and $\Delta Z_q$ are the differences along the z-axis between the slice plane $Z_r$ and points P and Q respectively and w is a weighting function 33 shown in FIG. 2(d) which varies linearly between zero and one for magnitudes of $\Delta Z_p$ and $\Delta Z_q$ between s and zero. The weighting function is generally triangular and linearly decreases the weight of a given projection with increasing distance from the slice plane. An entire projection set may be constructed for the slice plane $Z_r$ by using additional flanking points for other values of $\beta$.

Figure 2E:
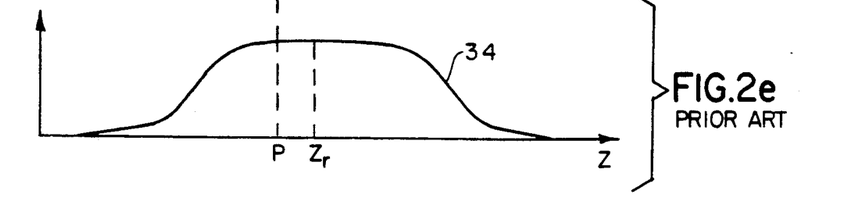
FIG. 2(e) is a graphical representation similar to FIG. 2(b) showing the effective slice profile of the fan beam of FIG. 1 after interpolation with the weighting function of FIG. 2(d)

The effect of the weighting function 33 is to produce an interpolated slice profile 34 substantially wider (with greater FWHM) than the slice profile 30. This results from the fact that the interpolated slice profile 34 will include data from slice profiles 30 taken over a z-axis range of 2s. This larger interpolated slice profile 34, arising from the interpolation required to reduce skew errors in helical scanning, detrimentally affects the z-axis resolution of the acquired projection data.

SUMMARY OF THE INVENTION

The present invention employs multiple narrow rows of detectors to generate a composite intensity signal having an effective profile, after interpolation for helical scanning, comparable to a non-interpolated fan beam in a stop and shoot CT system, without compromising the flexibility to choose any z-position for the reconstructed slice image.

Specifically, in a helically scanned system, an x-ray source produces a beam, along a beam axis, having rays both along the direction of translation of the patient and across the direction of translation of the patient. The x-ray source rotates about the patient while the patient is translated along the translation axis according to helical scanning techniques. A detector array receives the rays from the x-ray source after they pass through the patient.

The detector has a plurality of detector elements which are arranged in columns along the direction of translation and rows across the direction of translation. Each detector element produces a separate intensity signal dependent on the intensity of the ray received by that element. The separate intensity signals are selected according to their relationship to slice plane fixed with respect to the imaged object, combined and reconstructed into an image at the slice plane.

It is one object of the invention to reduce the effect of skew in helical imaging without decreasing the z-axis resolution of the scanning system or unduly slowing the scanning process. The use of multiple rows of detectors allows the helical pitch to equal the combined width of the detector array, and yet allows the span of interpolation to be limited to the width of a single row. If the total width of the combined rows is held equal to the desired slice thickness, the slice profile, even after interpolation, will remain essentially equal to the desired slice thickness.

The intensity signals from detector elements within a column across the rows, at a given gantry angle, may be combined with other elements from that column at that gantry angle or with elements from that column at gantry angles differing by an integer multiple of $\pi$. In one embodiment, the detector elements are selected so that the rays from which the interpolation is obtained are clustered symmetrically about the desired slice plane.

It is thus another object of the invention to provide maximum flexibility in selecting the slice plane after the acquisition of the projection data and to allow the spatially closest data to be used.

The combiner may simply add together the intensity values of a number of elements in a column at a given gantry angle, or other gantry angles differing by an integer multiple of $\pi$. The number of intensity signals may be equal to the number of elements in a column of the detector.

Thus, it is yet another object of the invention to permit the combination of intensity signals to provide improved signal-to-noise ratio.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

DETAILED DESCRIPTION OF THE PREFERRED EMBODIMENT

Figure 3:
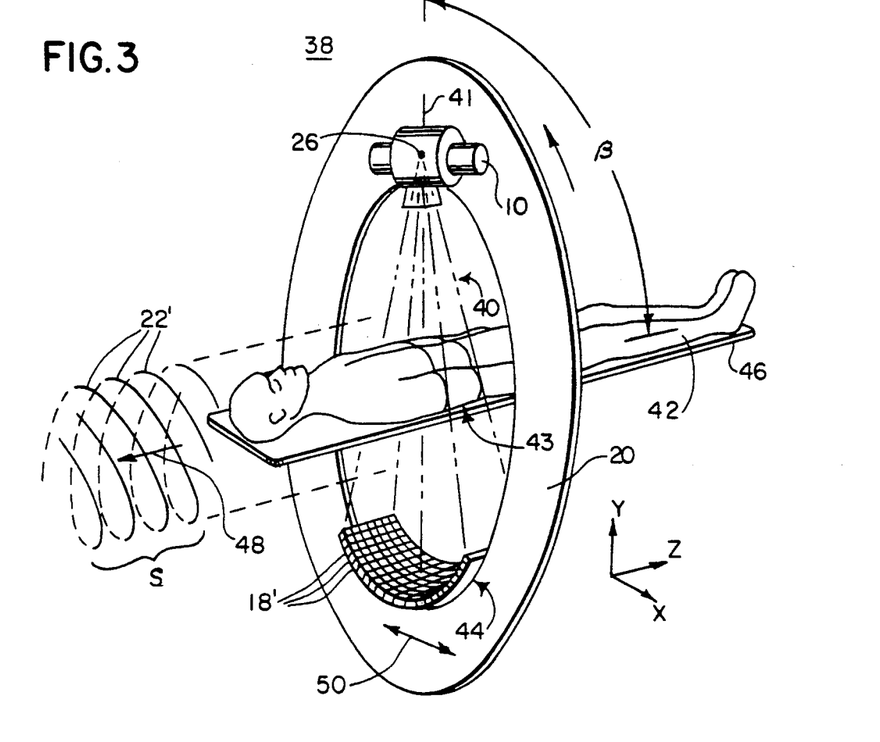
FIG. 3 is a pictorial representation of the CT apparatus of the present invention including a detector array having rows and columns of detector elements.

Referring to FIG. 3, a CT system for use with the present invention includes a gantry 20 supporting an x-ray source 10. The x-ray source 10 is oriented to project a cone beam 40 of x-rays along a beam axis 41 through a patient 42 to a supported and opposed detector array 44. The gantry 20 rotates to swing the beam axis 41 within a gantry plane 38 defining the x-y plane of a Cartesian coordinate system. Rotation of the gantry 20 is measured by angle $\beta$ from an arbitrary reference position within the gantry plane 38.

The patient 42 rests on a table 46 that may be moved along a translation axis 48 aligned with the z-axis of the Cartesian coordinate system. The table 46 may move across the gantry plane 38 and is radiotranslucent so as not to interfere with the imaging process.

The x-rays of the cone beam 40 diverge from the beam axis 41 and the gantry plane 38, along the translation axis 48, and also diverge from the beam axis 41 along the gantry plane 38 and along a transverse axis 50 generally orthogonal to both the beam axis 41 and the translation axis 48.

After passing through the patient 42, the x-rays of the cone beam 40 are received by the detector array 44 which, unlike the detector array 16 of FIG. 1, has multiple rows of detector elements 18'. The detector elements 18' are arranged in rows along the transverse axis 50 and in columns along the translation axis 48. At each gantry angle $\beta$, a separate projection is acquired by each row of the detector array 44, the projection including intensity signals from the detector elements 18' of that row. The surface of the detector array 44 describes generally a section of the surface of a sphere having a center at the focal spot 26.

The detector elements 18' each receive x-rays from the cone beam 40 and provide intensity measurements along separate rays of the cone beam 40. The intensity measurements together describe the attenuation of the cone beam 40 by a volume 43 of the patient 42. In the preferred embodiment, this measured volume 43 is substantially equal to the slice volume measured by a conventional fan beam CT system, and the width of the detector array 44, as measured along its columns, is approximately equal to the width of detector array 16 of FIG. 1. Accordingly, the columns of detector elements 18' simply subdivide a conventional wide fan beam detector array 16, such as shown in FIG. 1, along the z-axis.

Figure 4:
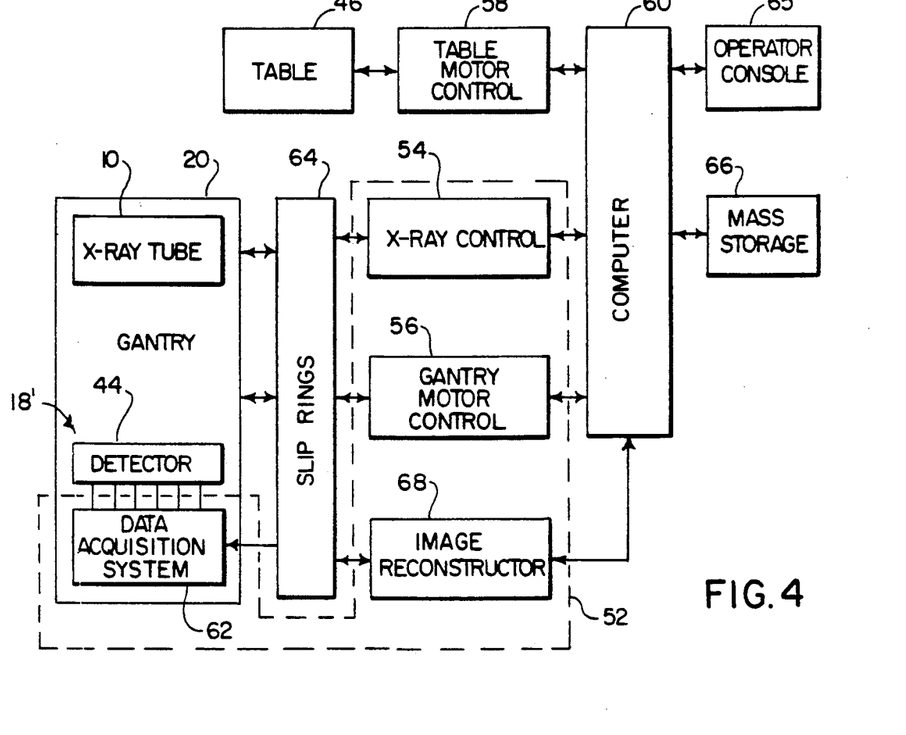
FIG. 4 is a block diagram of a CT control system that may be used with the CT apparatus of FIG. 3 and that is useful for practicing the present invention.

Referring to FIG. 4, the control system of the CT system of FIG. 3, has gantry associated control modules 52 which include an x-ray control 54, a gantry motor control 56, a data acquisition system 62 and an image reconstructor 68. The x-ray control 54 provides power and timing signals to the x-ray source 10 to turn it on and off under the control of a computer 60. The gantry motor control 56 controls the rotational speed and position of the gantry 20 and provides information to the computer 60 regarding gantry position. The data acquisition system 62 samples and digitizes intensity signals from the detector elements 18' of detector array 44, and the image reconstructor 68 receives the sampled and digitized intensity signals from the data acquisition system 62, each identified as to the row and column of the detector element 18' of the detector array 44, and combines the intensity signals from the detector elements 18' according to the present invention as will be described, and performs high speed image reconstruction according to methods known in the art.

Each of the above modules is connected to its associated elements on the gantry 20 via slip rings 64 and serves to interface computer 60 to various gantry functions. The slip rings 64 permit the gantry 20 to rotate continuously through angles greater than $2\pi$ radians to acquire projection data.

The speed and position of table 46 along the translation axis 48 is communicated to and controlled by computer 60 by means of table motor control 58. The computer 60 receives commands and scanning parameters via operator console 65, which is generally a CRT display, and keyboard which allows an operator to enter parameters for the scan and to display the reconstructed image and other information from the computer 60. A mass storage device 66 provides a means for storing operating programs for the CT imaging system, as well as for storing image data for future reference by the operator. Both the computer 60 and the image reconstructor 68 have associated electronic memory (not shown) for storing data.

During operation of the CT system, the gantry motor control 56 brings the gantry 20 up to rotational speed and the table motor control 58 begins translation of the table 46. The x-ray control 54 turns on the x-ray source 10 and projection data is acquired on a continuous basis. At each gantry angle $\beta$, the projection acquired includes intensity signals identified to each detector element 18' at each particular row and column of the detector array 44 and to a gantry angle $\beta$ and z-axis position.

Figure 5:
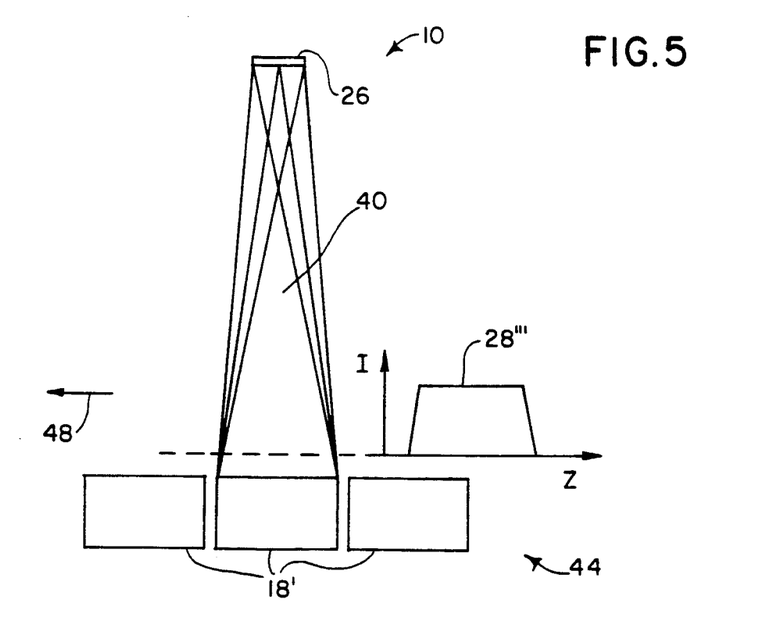
FIG. 5 is an exaggerated cross-section of a portion of the detector array of FIG. 3 and a portion of a fan beam showing the reduction of penumbra.

Referring now to FIG. 5, the use of multiple detector elements 18' in columns along the z-axis, or translation axis 48, substantially eliminates the penumbra 17 incident to the use of the blades of collimator 24 shown in FIG. 2(a). Each detector element 18' of a column is electrically independent and thus all but the detector elements 18' at the z-axis extremes of the columns, are self-collimating to the extent that the physical area of each detector element 18' serves to define the rays of the cone beam 40 to which it is sensitive rather than a separate collimator. Specifically, the face of the detector element 18', for all but the elements 18' at the extreme ends of the column, are unobstructed by a collimator to be fully illuminated by the entire area of the focal spot 26 eliminating any penumbra 17. This self-collimation substantially sharpens a rectangular intensity profile 28''' seen by each detector element 18', and the lack of a penumbra 17 is instrumental in allowing multiple detector elements 18' in each row of the detector array 44 without unduly reducing the practical working area of the detector array 44.

Referring now to FIGS. 6(a)-(d), the intensity profile 28''' is substantially narrower than the intensity profile 28' shown in FIG. 2(a). The intensity profile 28''' produces to a slice profile 30, shown in FIG. 6(b) having an FWHM of s' which, in the preferred embodiment, is significantly narrower than the FWHM s shown in FIG. 2(b) the latter being equal to the slice width of the CT system.

Figure 6A:
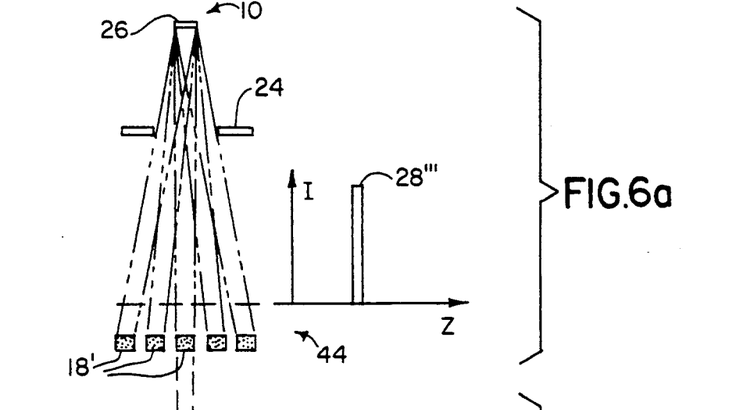
FIG. 6(a), is a cross-section of the entire fan beam and detector array of FIG. 5.
Figure 6B:
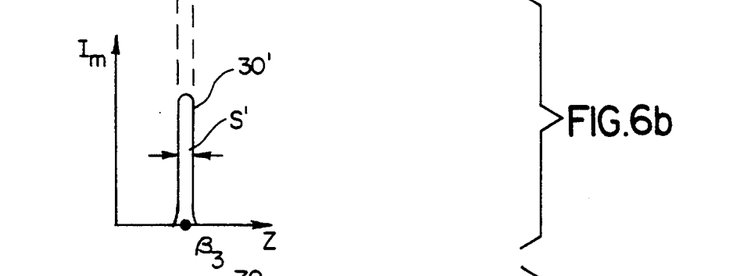
FIG. 6(b) is a graphical representation of the slice profile produced by the fan beam of FIG. 5(a) and a single detector element.
Figure 6C:
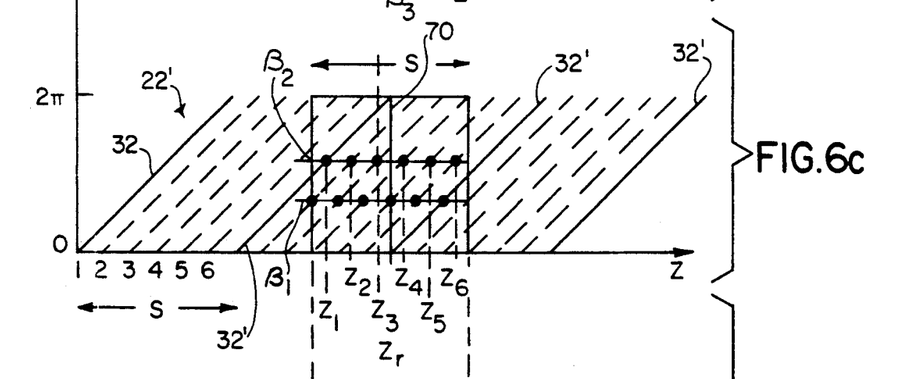
FIG. 6(c) is a graphical representation of the trajectory of each ray associated with a single detector element of FIG. 6(a), with helical scanning, along the z-dimension with increasing gantry angle $\beta$.

Referring now to FIGS. 3 and 6(c), the CT system of the present invention employs the same helical pitch of s employed by the system of FIG. 1, that is, for each full revolution of the gantry 20, the patient 42 is translated by an amount equal to a slice thickness s as shown by trajectory 32'. At each angle $\beta$ of the gantry 20, however, multiple intensity signals are obtained, displaced along the z-axis, from each detector element 18' within a column of the detector array 44. Thus, whereas in a conventional CT system, at each gantry angle $\beta$ a projection is acquired associated with a single point along the z-axis, in the present invention multiple thin projections are acquired associated with multiple contiguous points along the z-axis.

Referring to FIGS. 3 and 6(c), each detector element 18' within a column of the detector array 44 traces its own helix 22, having a pitch, s, essentially identical to the pitch of a conventional CT system but interleaved with the helices 22' of the other detector elements 18' within that column of detector array 44. Thus, the z-axis spacing at which projection data is acquired by adjacent detector elements 18', a column, is substantially less than s, i.e., less than the spacing at which projection data is acquired by detector elements 18 in consecutive scans of a conventional CT systems.

Accordingly, the interpolation of a projection for an arbitrary slice at position $Z_r$ may employ as few as two projections at points separated by as little as s' rather than s. As a result, the expansion of the effective beam profile caused by the interpolation to a slice plane at $Z_r$ is much reduced. Although, in principle, projections at only two points at z axis positions straddling the slice plane $Z_r$ are required to interpolate a projection at the slice plane $Z_r$, in the present embodiment, to provide adequate signal-to-noise ratio, multiple projections are used to generate a composite projection and interpolation, as such, is not used. Specifically, multiple projections are selected for each angle $\beta$ and combined to create the composite projection.

Projections are selected from multiple rows of the detector array 44 at a given gantry angle $\beta$ associated with positions proximate to $Z_r$ and/or from the projections at other gantry angles $\beta$ preceding or following the given gantry angle $\beta$ by $2\pi$ radians. For a detector array 44 having six rows and hence six detector elements 18' in each column, six projections are selected and clustered symmetrically on each side of the desired slice plane $Z_r$.

Referring to 6(c), at slice plane position $Z_r$, data must be collected for a full $2\pi$ of gantry rotation represented by projection set line 70. For example, a composite projection may be generated at slice plane $Z_r$ and gantry angle $\beta_2$ by summing together the projections from the first, second, third, fourth, fifth and sixth rows of the detector array 44 corresponding to z-axis location $Z_1$, $Z_2$, $Z_3$, $Z_4$, $Z_5$, and $Z_6$, all at one gantry angle. For a preceding gantry angle of $\beta_1$, however, the helical movement of the gantry 20 moves the z-axis location of the detector array 44, so that its rows are no longer symmetrically clustered about the z-axis position of the slice plane $Z_r$. Accordingly, the projections from the second, third, fourth, fifth and sixth rows of the detector array 44 at the gantry angle $\beta_1$ are employed and the projection from the first row of the detector array 44 at gantry position $\beta_1 + 2\pi$. The z-axis locations for the projections at gantry angles $\beta_1$ and $\beta_1 + 2\pi$ will in generally not align with the positions $Z_1$-$Z_6$ of gantry angle $\beta_2$ but the difference is small and may be ignored for the combined data.

The operation of the above described selection of projections during helical scanning results in the projections from rows, at one end of the detector array 44, being dropped in favor of the projections from rows at gantry angles $2\pi$ greater. The intent is to have the multiple z-axis positions of the projections close to the position of the slice plane $Z_r$.

Figure 6D:
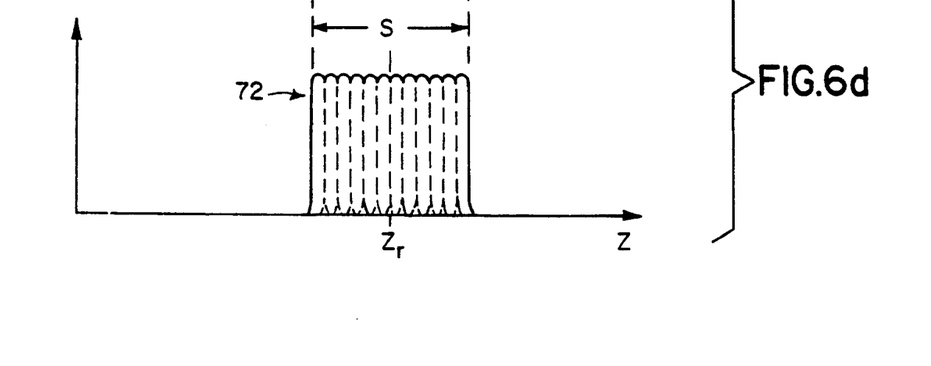
FIG. 6(d) is a graphical representation similar to FIG. 6(b) showing the effective slice profile of the fan beam of FIG. 6(a) after combining a number of single detector elements.

The projections from the multiple rows of detector array 44 are added together rather than interpolated, the adding having the effect of broadening the effective slice profile s' of individual detector element 18' of the projections to a composite slice profile 72 shown in FIG. 6(d). This composite slice profile 72 has a FWHM approximately equal to s and thus comports with the desired spatial resolution of the CT system and represents a clear advance over the slice profile provided by conventional CT helical scanning with interpolation. A composite projection being the sum of the selected projections is processed by the CT system per a conventional CT reconstruction techniques and implicitly is filtered for aliasing, per those techniques, on the basis of a slice thickness s.

The summing of the multiple projections together without regard to differences in their z-axis position reflects the fact that the breaking of the detector array 44 into multiple rows of detector elements 18' is not primarily intended to decrease the size of the slice thickness but to improve the wider slice profiles. Summing of multiple projections from the multiple rows of detector elements 18' forms a composite projection reflecting that signal intensity that would be received by a single row of detector elements, such as provided in prior art CT systems, under the stop and shoot methodology but permits the speed increases attendant to helical scanning.

Thus, the effect of the invention is to prevent the spreading of the effective slice profile produced by the CT apparatus and typically incident to helical scanning.

It should be noted that the apparatus of the present invention provides other incidental benefits attendant to the multiple row detector element. If extremely narrow detectors permit simultaneous acquisition of the necessary narrow projections without decreasing the pitch of the helical acquisition. The multiple narrow projections from the rows detector may also be used to reduce partial volume artifacts as described in co-pending application Ser. No. 07/813,222 filed Dec. 23, 1991, entitled: "Segmented Detector for Computer Tomography Scanner, assigned to the same assignee as the present invention, and hereby incorporated by reference into this specification.

Many modifications and variations of the preferred embodiment which will still be within the spirit and scope of the invention will be apparent to those with ordinary skill in the art. First, the techniques of "half scanning", which recognizes an equivalence between rays of projections acquired along angles separated by only $\pi$ radians may be used with the above techniques allowing combinations of detector signals at ray angles differing by as little as integral multiples of $\pi$. Different gantry angles where the columns of the detector 44 provide intensity signals along parallel rays will be termed "related angles". Second, although in the preferred embodiment, the detector elements are laid out in rectilinear rows and columns it will be recognized from the description of the invention, that the columns and rows need not be in straight lines so long as intensity signals along multiple rows may be measured. In order to apprise the public of the various embodiments that may fall within the scope of the invention, the following claims are made:

I claim:

1. A computed tomography apparatus producing images of an imaged object and comprising:

an x-ray source directing an x-ray beam along a beam axis with movement of the beam axis throughout a plurality of beam angles about a translation axis, the x-ray beam including a plurality of rays spaced in two dimensions with respect to the beam axis first along the translation axis with respect to the beam axis and second along a transverse axis perpendicular to the translation axis;

an array of detector elements receiving the x-ray beam after it passes through the imaged object, the detector elements arranged in columns along the translation axis and rows along the transverse axis, each detector element producing an intensity signal dependent on the intensity of the ray of x-ray associated with the detector element;

a translator for moving the imaged object along the translation axis with respect to the x-ray source throughout a plurality of translation positions during the movement of the beam axis throughout the plurality of beam angles;

a combiner receiving the intensity signals and combining the intensity signals from at least one detector element in each column at a given beam angle, and at least one detector element in a corresponding column at a beam angle related to the given beam angle, the detector elements having a predetermined relationship with respect to a slice plane stationary with the imaged object and the combined intensity signals from the detector elements in each column producing a corresponding composite intensity signal associated with the slice plane; and a display means receiving the composite intensity signals and displaying an image of the imaged object at the slice plane from the composite intensity signals.

2. The computed tomography apparatus of claim 1 wherein the combiner is an adder which takes the arithmetic sum of the intensity signals from the detector elements.

3. The computed tomography apparatus of claim 1 wherein the combiner receives intensity signals from detector elements which corresponding to rays closest to the slice plane.

4. The computed tomography apparatus of claim 1 wherein the combiner combines the intensity signals from a number of detector elements substantially equal to the number of detector elements in one column.

5. A method of producing images of an imaged object comprising the steps of:

generating an x-ray beam from an x-ray source along a beam axis, the x-ray beam including a plurality of rays spaced in two dimensions with respect to the beam axis first along the translation axis in columns and second along a transverse axis perpendicular to the translation axis in rows;

moving the beam axis throughout a plurality of beam angles about the translation axis;

receiving the x-ray beam after it passes through the imaged object at a plurality of detector elements in columns along the translation axis, each detector element receiving a ray to produce an intensity signals associated with each ray;

translating the imaged object along the translation axis with respect to the x-ray source during the moving of the beam axis throughout the plurality of beam angles;

combining the intensity signals from at least one detector element in each column at a given beam angle, and at least one detector element in each of corresponding columns at a beam angle related to the given beam angle, the detector elements having a predetermined relationship with respect to a slice plane stationary to the imaged object, to produce corresponding composite intensity signals associated with the slice plane; and displaying an image of the imaged object at the slice plane from the composite intensity signals.

6. The method recited in claim 5 wherein the step of combining the intensity signals takes the arithmetic sum of the intensity signals from the detector elements.

7. The method recited in claim 5 wherein the step of combining the intensity signals combines those intensity signals from detector elements which correspond to rays closest to the slice plane.

8. The method recited in claim 5 wherein the step of combining the intensity signals combines the intensity signals from a number of detector elements substantially equal to the number of elements in one column.

* * * * *